(12) United States Patent
Massoni

(10) Patent No.: US 7,097,668 B2
(45) Date of Patent: Aug. 29, 2006

(54) TEMPORARY HAIR DYE COMPOSITION

(75) Inventor: Jack Massoni, New Fairfield, CT (US)

(73) Assignee: Combe Incorporated, White Plaines, NY (US)

( * ) Notice: Subject to any disclaimer, the term of this patent is extended or adjusted under 35 U.S.C. 154(b) by 0 days.

(21) Appl. No.: 10/244,275

(22) Filed: Sep. 16, 2002

(65) Prior Publication Data
US 2004/0055094 A1    Mar. 25, 2004

(51) Int. Cl.
*A61K 7/13*    (2006.01)
(52) U.S. Cl. .................. 8/405; 8/426; 8/435; 8/454; 8/455; 8/509; 8/552; 8/558; 8/604
(58) Field of Classification Search .............. 8/405, 8/426, 435, 454, 455, 509, 552, 558, 604
See application file for complete search history.

(56) References Cited

U.S. PATENT DOCUMENTS

| | | | |
|---|---|---|---|
| 4,065,255 A | 12/1977 | Andrillon et al. ............ 8/110.2 |
| 4,114,632 A | 9/1978 | Morganroth .................... 132/7 |
| 4,182,612 A | 1/1980 | Sokol et al. ................. 8/110.1 |
| 4,270,916 A * | 6/1981 | Racciato ........................ 8/527 |
| 5,173,085 A | 12/1992 | Brown et al. .................. 8/405 |
| 5,192,332 A | 3/1993 | Lang et al. ..................... 8/405 |
| 5,224,964 A | 7/1993 | Shami ........................... 8/405 |
| 5,281,240 A | 1/1994 | McGee ......................... 8/405 |
| 5,645,609 A | 7/1997 | Andrean et al. ............... 8/405 |
| 5,688,291 A | 11/1997 | Said et al. ..................... 8/431 |
| 5,733,344 A | 3/1998 | Shiraishi et al. ............... 8/435 |
| 6,123,952 A | 9/2000 | Lagrange .................... 424/401 |
| 6,303,794 B1 | 10/2001 | Guth et al. .................. 548/547 |
| 6,312,478 B1 | 11/2001 | Goettel et al. ................. 8/405 |
| 6,371,994 B1 | 4/2002 | Lang et al. ..................... 8/426 |
| 2002/0194683 A1* | 12/2002 | Casperson et al. ............. 8/405 |

FOREIGN PATENT DOCUMENTS

| | | | |
|---|---|---|---|
| EP | 1 142 560 A2 | * | 10/2001 |
| GB | 2001678 A | * | 2/1979 |
| JP | 55157602 A | * | 12/1980 |

* cited by examiner

*Primary Examiner*—Eisa Elhilo
(74) *Attorney, Agent, or Firm*—James V. Costigan; Hedman & Costigan, P.C.

(57) ABSTRACT

A temporary hair dyeing composition which comprises:
(a) a cationic dye;
(b) a water soluble anionic polymer; and
(c) water.

2 Claims, No Drawings

TEMPORARY HAIR DYE COMPOSITION

BACKGROUND OF THE INVENTION

The coloring of human hair has been practiced in various forms for thousands of years. In the last century these practices have evolved into three general types of haircolor: permanent, semi-permanent, and temporary. The term "permanent" refers to oxidative dying systems that permanently alter the hair's coloration. Reapplication occurs as the hair's new growth becomes noticeable. Oxidative hair dyes are usually sold in the form of a two-component kit. In one container is an aqueous alkaline composition that contains oxidative dyes and an appropriate vehicle. In the other container is a developer composition that has an oxidizing agent, usually hydrogen peroxide. The two compositions are mixed immediately prior to use and applied to the hair. The high pH of the mixture causes the hair shaft to swell, allowing the dye precursors to penetrate into the hair shaft. These dye precursors are oxidized, which combine to form larger molecules with color in the interior of the hair shaft. After an appropriate development time, the mixture is rinsed from the hair. The color of the hair is then permanently altered. This is the most popular form of haircolor for both men and women, as the results can be very natural looking and require maintenance only every 4–6 weeks.

Semi-permanent haircolor uses so-called preformed dye molecules that are not mixed with a developer prior to application. Therefore the size of the molecules does not change during the dye process. Semi-permanent dyes will wash out of the hair after six to twelve shampooings. Since no permanent change occurs to the hair's coloration, a natural looking blending of gray and pigmented hair can occur. The drawback with this type of a dye is that it exhibits a lack of durability and the development of off-tones that don't mimic the original color of the hair.

Temporary haircolor is applied to the hair surface, and is generally removed with one shampoo. Traditionally, these are used when a cosmetic effect is desired for one day.

Most products marketed use some type of insoluble pigment such as iron oxides, certified dye lakes, or titanium dioxide coated micas. They are contained in a styling gel media or some other appropriate vehicle that is often similar to mascara or other topical cosmetic. The drawbacks of these products are that they can only be useful for highlighting selected strands of hair to achieve a dramatic look. They are not practical when a natural allover color is desired as the compounds impart a "painted-on" appearance. Attempts have been made to improve the adherence of these pigments to the hair surface by using unique polymer compositions such as those disclosed in U.S. Pat. No. 6,042,619. More natural looking temporary hair colors were described in U.S. Pat. No. 5,454,841. These formulations incorporate a mixture of synthetic melanin with cationic surfactants in order to temporarily adhere the pigment to the hair. The expense and unavailability of the melanin makes these formulations impractical for commercial use. In addition the shade range is very limited for such a product, as melanin only permits the formulation of a black temporary hair color.

Manufacturers of haircoloring products have searched for temporary products that replicate the natural results achieved by a permanent haircolor, while having the feature of removability with one shampooing. The objective has been to provide what can be called a temporary hair color that can be used to preview a particular shade of color for determining the acceptability of the color or to provide an extreme hair color dye that can be used for theatrical purposes or for special occasions where extreme hair color of a temporary nature is desired.

The "try-on" concept for a particular haircolor that accurately mimics the permanent product would allow a consumer to preview haircolor without being concerned about the ease of complete removability with an ordinary shampoo. The "try-on" product would only be practical for the permanent haircolor subcategory of "demi-permanent" or "deposit only permanent". These specialized colorants the permanent products are modified using reduced alkali levels that will essentially prevent the alteration of the hair's natural pigment. This lack of lightening of the natural pigment gives rise to a category that blends gray for a very natural appearance more like a semi-permanent color, but with all of the permanent advantages. These include durability and wearing on tone. Although this subcategory remains small for women's haircolor because it does not allow for the creation of blonde shades or the ability to make one's hair lighter, the majority of men's haircolorants rely on this technology. Realistic looking temporary haircolors have been devised by synthesizing fixative like polymers where the actual color moiety is included in the molecules such as those described in U.S. Pat. Nos. 5,735,907 and 5,876,463. The performance of these materials is acceptable for use in "try-on" products, however the complex nature of their manufacture and the expense involved has prevented commercialization of these formulation.

The applicant has found that a complex of a cationic dye and a water-soluble anionic polymer will provide a dye complex which may be dispersed in suitable vehicle to provide temporary hair color.

SUMMARY OF THE INVENTION

The invention comprises a temporary hair dye which is based on a complex formed by a combination of cationic dye materials with water-soluble anionic polymers. This dye complex is dispersed in a suitable cosmetic vehicle. Upon application to the hair, the product will spread evenly on the surface leaving a temporary coating of color. This composition leaves a more translucent coating on the hair than insoluble pigments such as iron oxides and micas. The resulting color most resembles an oxidation haircolor in finished appearance.

It is therefore a primary object of this invention is to provide a practical composition of commercially available materials that will create a temporary haircoloring product with acceptable properties for use as a "try-on" haircoloring product.

It is also an object of the invention to provide a method for coloring hair with a composition containing these materials and a manufacturing procedure for preparation of these compositions.

DERAILED DESCRIPTION OF THE INVENTION

The cationic dye materials used should have a favorable toxicological profile. They include compounds such as: Basic Blue 99, Basic Brown 17, Basic Brown 16, Basic Red 76, Basic Yellow 57, Basic Red 51, Basic Yellow 87 and Basic Orange 31. These material are well known and they are commercially available.

The cationic dyes have a relatively large molecular size when compared to other haircolor dyes and would not normally penetrate below the surface of individual hairs to any appreciable degree. Because these cationic dyes have a positive charge on the molecule they readily attach themselves to the surface of the hair that carries a negative charge. These cationic dyes by themselves act like semi-permanent haircolors, and could require multiple shampooings to remove from the hair. When the cationic dyes are pre-complexed dyes with an anionic polymer, the resulting compounds are no longer semi-permanent dyes, but have the property of providing natural or if desired, extreme looking temporary haircolor. These haircolors are suitable for "try-on" products which can be sampled to potential customers to allow coloring of the hair with a haircolor that can easily be removed by shampooing.

The water-soluble anionic polymers used are cosmetically acceptable materials that usually require neutralization using some type of alkali to form the negative charge on the polymer. These are normally used to thicken a variety of commercially available compositions. The thickening property imparts thickening to the vehicle used in the present invention. The anionic polymers include sodium alginate, carbomers (acrylic acid polymers), acrylates/steareth-20 itaconate copolymer, acrylates/ceteth-20 itaconate copolymer, acrylates/CIO-30 alkyl acrylate crosspolymer, acrylate/steareth-20 methacrylate copolymer, steareth-10 allyl ether/acrylates copolymer, acrylates/ceteth-20 methacrylates copolymer, acrylates/palmeth-25 methacrylates copolymer, acrylates/palmeth-25 acrylate copolymer, acrylates/steareth-50 acrylate copolymer, acrylates/vinyl isodecanoate crosspolymer, acrylic acid/acrylonitrogens copolymer, algin, sodium acrylates/vinyl isodecanoate crosspolymer, starch polyacrylonitrile copolymer (sodium or potassium salt), TEA acrylates/acryonitrile copolymer and other similar materials.

The hair color of the invention may also contain auxiliary thickeners such as fatty esters and fatty alcohols and/or low levels of nonionic surfactants to aid in product spreadability, preservatives, dye solvents, conditioners, fixatives, and fragrances.

The formation and usefulness of the cationic dye/anionic polymer complex is illustrated in Example 1 which contains both the cationic dyes and anionic polymer. Comparative Example 1 has no anionic polymer and no alkali to neutralize the polymer, and Comparative Example 2 has no anionic polymer.

EXAMPLE 1

| Ingredient | Function | Wt % |
|---|---|---|
| Water (deionized) | solvent | 86.140 |
| Acrylates/Ceteth-20 Itaconate Copolymer | anionic polymer | 3.000 |
| PEG Glyceryl Cocoate | surfactant | 3.000 |
| Glyceryl stearate Laureth-23 | thickener | 3.500 |
| Polysaccharide resin | fixative | 2.000 |
| Aminomethyl propanol | alkalizer | 0.400 |
| Diazolidinyl urea | preservative | 1.000 |
| Polysiloxy linoleyl Pyrolidone | conditioner | 0.500 |
| Fragrance | | 0.200 |
| Basic Brown 17 | Cationic dye | 0.030 |
| Basic Blue 99 | Cationic dye | 0.150 |
| Basic Brown 16 | Cationic dye | 0.080 |
| pH 7.5 | | |

Comparative Example 1

| Ingredient | Function | Wt % |
|---|---|---|
| Water (deionized) | solvent | 89.540 |
| Acrylates/Ceteth-20 Itaconate Copolymer | anionic polymer | 0 |
| PEG Glyceryl Cocoate | surfactant | 3.000 |
| Glyceryl stearate Laureth-23 | thickener | 3.500 |
| Polysaccharide resin | fixative | 2.000 |
| Aminomethyl propanol | alkalizer | 0 |
| Diazolidinyl urea | preservative | 1.000 |
| Polysiloxy linoleyl Pyrolidone | conditioner | 0.500 |
| Fragrance | | 0.200 |
| Basic Brown 17 | Cationic dye | 0.030 |
| Basic Blue 99 | Cationic dye | 0.150 |
| Basic Brown 16 | Cationic dye | 0.080 |
| pH 7.2 | | |

Comparative Example 2

| Ingredient | Function | Wt % |
|---|---|---|
| Water (deionized) | solvent | 89.140 |
| Acrylates/Ceteth-20 Itaconate Copolymer | anionic polymer | 0 |
| PEG Glyceryl Cocoate | surfactant | 3.000 |
| Glyceryl stearate Laureth-23 | thickener | 3.500 |
| Polysaccharide resin | fixative | 2.000 |
| Aminomethyl propanol | alkalizer | 0.400 |
| Diazolidinyl urea | preservative | 1.000 |
| Polysiloxy linoleyl Pyrolidone | conditioner | 0.500 |
| Fragrance | | 0.200 |
| Basic Brown 17 | Cationic dye | 0.030 |
| Basic Blue 99 | Cationic dye | 0.150 |
| Basic Brown 16 | Cationic dye | 0.080 |
| pH 9.8 | | |

Manufacturing Procedure:

The total amount of water for the formulation is added to the batch vessel with the anionic polymer. With agitation the mixture is heated to 60° C. and then neutralized with aminomethyl propanol(if present). The mixture will clear and thicken. To a separate container the remaining water and PEG-7 Glyceryl Cocoate, Glyceryl Stearate & Laureth-23, and the polysaccharide resin are added and heated to 70° C. with mixing. The dyes are dissolved in this mixture and maintained at 70° C. for 30 minutes. The dye premix is slowly added to the main batch tank. The mixture is cooled to 40–45° C. and the preservative, fragrance, and conditioner are added The batch is mixed for an additional 5 minutes and filled into suitable containers.

For comparative examples 2 & 3, the total water, PEG-7 Glyceryl Cocoate, Glyceryl Stearate & Laureth-23, Polysaccharide Resin, and all of the dyes are added to the batch vessel and heated to 70° C. with agitation. Upon dissolution of the dyes, the batch is cooled to 40–45° C. The aminomethyl propanol (for comparative example 2 only), preservative, fragrance, and conditioner are added. The batch is mixed for an additional 5 minutes and filled into suitable containers.

Test Procedure:

Swatches (3 grams) were prepared from human 90% gray hair. These swatches were dampened with deionized water and blotted to remove the excess. All of the formulas were applied to individual" swatches by working in 1 gram of product manually until all fibers were saturated. The excess product was blotted. It should be noted that example 1 produced no skin staining, while comparative examples 1 and 2 had profuse skin staining. The swatches were dried with a hair dryer. The color was measured on an untreated swatch and on the three formulas using a Minolta Spectrophotometer, Model No. CM-508d. As is the industry standard, the Hunter L,a,b scale was used where "L" is the lightness (+ lighter, – darker), "a" indicates relative amounts of red (+) or green (–), and "b" indicates relative amounts of yellow (+) or blue (–). E (total color value) can be calculated as E=(L2+a2+b1)1/2, and consequently delta E is the total color change between treatments. The treated swatches were shampooed with a commercially available product, dried, and the color measurement was repeated. The results are illustrated in FIG. 1, and clearly show that example I with the cationic dye/anionic polymer complex is completely removed by shampooing once. Comparative examples 1 & 2, where only the cationic dye is present in the formula, indicate that significant amounts of color remain on the hair after one shampooing as would be expected from a semi-permanent haircolor. The combination of dye and polymer unexpectedly act as a temporary colorant (insoluble pigment), while maintaining the sheer appearance of a soluble dyestuff. The resulting color of example 1 is acceptable for use as a "try-on" product or temporary extreme color that replicates a deposit-only permanent haircolor.

Minolta Spectrophotometer readings for light brown formulas

| | Control | Ex. 1 | Ex. 1 | C. Ex. 1 | C. Ex. 1 | C. Ex. 2 | C. Ex. 3 |
|---|---|---|---|---|---|---|---|
| | (Gray) | Treated | Shampoo | Treated | Shampoo | Treated | Shampoo |
| L = | 47.3 | 35.7 | 47.9 | 31.6 | 37.8 | 28.8 | 34.9 |
| a = | 0.7 | 2.9 | 0.9 | 3.6 | 2.3 | 3.5 | 2.2 |
| b = | 8.0 | 6.3 | 8.8 | 3.5 | 6.8 | 6.4 | 6.2 |
| | | | Delta E 12.6 | | Delta E 6.4 | | Delta E 6.2 |

The laboratory performance of example 1 and other shades using a similar vehicle were confirmed by salon testing of the formulations on human clients. The clients had between 25 and 100% gray hair with varying depth of pigmented hair. All participants in the experiment had no haircoloring product remaining in their hair at the time of application. As with the swatches the hair was dampened before product application. The hair colors were then applied to a comb and combed onto the hair. The hair was dried and examined for coverage, tone, and depth. The hair was then shampooed. In 30 people tested, all of the color was completely removed.

A second set of salon experiments was devised to evaluate the "sheerness" or "natural look" of the try-on formulations. In these cases the try-on product was applied to half of the head only in the same manner as the first experiment. Prior to the application of the temporary colorant, a deposit only permanent product of the same shade type was applied to the opposite side of the head for the prescribed time, rinsed, shampooed, and dried.

The two colors were examined blind by a panel of three expert color evaluators, in all cases the temporary and permanent colors gave natural looking results with no flat, matte or "painted-on" appearances. No expert could visually determine which product was permanent, and which was the temporary.

Other useful formulas that were explored are shown in examples 2–5.

| Ingredients | Function | Dark Blonde Ex. 2 | Medium Brown Ex. 3 | Dark Brown Ex. 4 | Black Ex. 5 |
|---|---|---|---|---|---|
| Deionized Water | solvent | 92.680 | 94.035 | 90.080 | 86.750 |
| Carbomer (Ultrez 10) | anionic polymer | 1.000 | 0 | 0 | 0 |
| Sodium alginate | anionic polymer | 0 | 1.000 | 0 | 0 |
| Steareth-10 allyl ether | anionic polymer | 0 | 0 | 3.00 | 0 |
| Acrylates C 10–30 alkly-acrylate crosspolymer | anionic polymer | 0 | 0 | 0 | 2.500 |
| Polysorbate 20 | surfactant | 0 | 1.000 | 0 | 0 |
| Methyl/propyl paraben | preservative | 0.500 | 0 | 0 | 0 |
| PVP/PVA | fixative | 0 | 3.000 | 0 | 0 |
| PVP | fixative | 0 | 0 | 2.000 | 2.000 |
| Fragrance | | 0.200 | 0.200 | 0.200 | 0.200 |
| Steareth-21 | surfactant | 0.050 | 0 | 0 | 0 |
| Laureth-23 | surfactant | 0 | 0 | 2.000 | 0 |
| Ethoxydiglycol | dye solv. | 5.000 | 0 | 0 | 0 |
| Propylene glycol | dye solv. | 0 | 0 | 0 | 5.000 |
| Basic blue 99 | cat. dye | 0 | 0.100 | 1.000 | 3.000 |
| Basic Brown 17 | cat. dye | 0.050 | 0.080 | 0.500 | 0.500 |
| Basic Brown 16 | cat. dye | 0 | 0.080 | 0.500 | 0 |
| Basic Red 57 | cat. dye | 0.010 | 0 | 0.020 | 0 |
| Basic Yellow 57 | cat. dye | 0.010 | 0.005 | 0 | 0 |
| Ethanolamine | alkalizer | 0.500 | 0.500 | | |
| 50% solution NaOH | alkalizer | 0 | 0 | 0 | 0.050 |
| Triethanolamine | alkalizer | 0 | 0 | 0.700 | 0 |

The composition of the invention preferably comprises the following ingredients in percent by weight based on the total weight of composition:

0.001–10% or preferably 0.01–4 of a cationic or basic dye compound;

0.1–10% or preferably 0.5–5% of a water soluble anionic polymer;

0.1–10% or preferably 1–5% of alkalizer;

75–99% or preferably 75–99% water.

The pH of the composition may be adjusted to a pH in the range of 6–10 or more preferably a pH of 7–8.5.

Obvious modifications or variations are possible in light of the above teachings. All such obvious modifications and variations are intended to be within the scope of the appended claims.

The compositions of the invention may contain one or more additional ingredients in effective amounts to improve the aesthetic properties of the compositions, such as thickening agents, surfactants to aid in the spreading characteristics, preservatives, dye solvents, fragrances, fixatives to aid in dye adhesion to the hair and conditioning agents.

I claim:

1. A method of temporarily dyeing hair which comprises applying a composition which consists of the following ingredients in weight percent based on the total weight of the temporary hair color composition:
   (a) 0.001–10% of a cationic dye;
   (b) 01–10% of a water soluble anionic polymer;
   (c) 0.1–10% of an alkalizer; and
   (d) 75–99% water.

2. A temporary hair dyeing composition which consists of the following ingredients:
   (a) a cationic dye;
   (b) a water soluble anionic polymer;
   (c) an alkalizer; and
   (d) water wherein said composition is prepared by first combining the water soluble anionic polymer with the alkalizer and water to form a neutralized water soluble anionic polymer and thereafter combining the neutralized water soluble anionic polymer with the cationic dye to form said temporary hair dyeing composition.

* * * * *